United States Patent
Grinstead et al.

(12) 
(10) Patent No.: US 7,246,628 B1
(45) Date of Patent: Jul. 24, 2007

(54) METHOD FOR CLEANING FLOOR DRAINS

(75) Inventors: Dale Albert Grinstead, Racine, WI (US); James H. Wilson, Jr., Fort Mill, SC (US); Thomas H. Beinkemper, Doylestown, PA (US)

(73) Assignee: JohnsonDiversey, Inc., Sturtevant, WI (US)

( * ) Notice: Subject to any disclaimer, the term of this patent is extended or adjusted under 35 U.S.C. 154(b) by 0 days.

(21) Appl. No.: 11/358,175

(22) Filed: Feb. 21, 2006

(51) Int. Cl.
*C09K 3/30* (2006.01)
*B05B 9/04* (2006.01)
*C11D 3/00* (2006.01)

(52) U.S. Cl. .................. 134/167 C; 510/379
(58) Field of Classification Search ............. None
See application file for complete search history.

(56) References Cited

U.S. PATENT DOCUMENTS 6,197,321 B1 * 3/2001 Richter et al. ............. 424/409
6,635,676 B2 * 10/2003 Baker et al. ................ 514/642
6,927,237 B2 * 8/2005 Hei et al. ................... 514/557
7,063,095 B2 6/2006 Barcay et al. .............. 134/166

FOREIGN PATENT DOCUMENTS

JP 02-175800 7/1990

* cited by examiner

*Primary Examiner*—Douglas McGinty
*Assistant Examiner*—John M. Petruncio
(74) *Attorney, Agent, or Firm*—Neil E. Hamilton; James J. Sales; Gregory S. Bollis

(57) ABSTRACT

A method for controlling *Listeria* in floor drains wherein an aqueous solution composed of a chlorinated caustic material which is soft metal compatible is introduced into a drain where *Listeria* is present. In a preferred manner, the aqueous solution is introduced into the drain employing a hose end dispensing device having a foam producing nozzle. The resulting aqueous solution has a sufficient viscosity to remain in the drain for about 30 seconds to 10 minutes.

11 Claims, 3 Drawing Sheets

METHOD FOR CLEANING FLOOR DRAINS

CROSS-REFERENCE TO RELATED APPLICATIONS, IF ANY

Not applicable.

STATEMENT REGARDING FEDERALLY FUNDED RESEARCH

Not applicable.

BACKGROUND OF THE INVENTION

1. Technical Field

This invention relates to a method for cleaning floor drains. More particularly, it relates to a method for reducing the amount of *Listeria* in floor drains.

2. Background Art

Cleaning devices and formulations which are especially formulated for cleaning floor drains are known. For example, Ecolab Pathways Drain Ring available from Ecolab, Inc. in St. Paul, Minn.; CRS Power Strips available from Supply Systems of Dallas, Tex. and Spartan Chemical Consume Drop-In-A-Drain in Maumee, Ohio.

*Listeria* control is a critical issue for food retail customers. *Listeria monocytogenes* has three characteristics that make it a serious food safety concern. One of these characteristics is its ability to grow at refrigeration temperatures. Most food borne pathogens do not grow at all at refrigeration temperatures. Although *Listeria* grows slowly at low temperatures, it can grow to high levels given enough time. This means that just a few cells contaminating a food that will not be further cooked prior to eating it can, given enough time, grow to millions of cells, even if the food is kept refrigerated.

The second reason that *Listeria* is a food safety concern is that the organism is so common in the environment. It can be isolated from soil, plants, and many species of animals and birds. Because it is such a common organism, it is virtually impossible to keep *Listeria* out of a food retail setting where customers, employees, and equipment are moving in, out, and around the store throughout a day. If the organism finds its way into a niche where the environment is favorable and there is a source of food and water, it can colonize that location and grow to high levels. It is possible for the organism to then spread from that location to food contact surfaces like slicers, cutting boards, or hands and so contaminate food. It will grow at refrigeration temperatures and may be found in many locations in a retail setting. It takes a relatively high number of cells to have a high risk of causing disease so the key to controlling this disease is not to let the organism grow to high levels in the food or a food retail setting. One way of controlling this disease is by good cleaning programs.

The final reason that there is so much attention given to *Listeria* is that the disease it causes is very serious. The mortality rate for Listeriosis is approximately 20%–25%. Although *Listeria* generally causes a relatively minor illness that is often mistaken for the flu in healthy adults, in an individual that is immune compromised, the illness it causes can be far more serious. Immune compromised individuals are those whose immune systems are not fully functional. This can include the very young and very old, people that have other underlying illness like diabetes or cancer, pregnant women, or someone that is recovering from some surgical procedures such as a transplant. Immune compromised individuals are far more likely to develop complications from listeriosis like septicemia, meningitis, encephalitis, endocarditis, and spontaneous abortion. Many of the complications can result in death.

Given the nature of *Listeria* and the disease it causes, it is not surprising that retail customers are concerned about controlling this organism. Floor drains are a specific environment within a retail setting that is frequently cited as a potential reservoir for this organism. A floor drain provides a very favorable location for *Listeria* to grow. There is a lot of food and water present in most floor drains. *Listeria* can form biofilms that can attach to surfaces and many floor drains have very high surface areas. In many retail food stores, floor drains are cleaned infrequently so the organism has time to establish itself and grow to high levels.

Previous Studies

A study was conducted that examined floor drains and methods to control *Listeria* in them indicated that sanitizers may not be the best way to control pathogens in this environment. That study found that *Listeria* was present in approximately half of the drains tested. The level of *Listeria* was generally low, from one to two $\log_{10}$ colony forming unit (CFU). Aerobic Plate Counts (APCs) showed that the total level of microorganisms on the drains was from 4–8 $\log_{10}$ CFU. During this study two sanitizers were tested. A quat based sanitizer was tested at 200 and 400 PPM as well as a 10 PPM solution of chlorine dioxide. None of the tested sanitizers achieved much reduction. The chlorine dioxide was able to reduce but not eliminate the *Listeria* and the quat had a very small effect (ca. 0.3 to 0.5 reduction in $\log_{10}$ CFU).

The relatively poor performance of the sanitizers tested in this study was possibly the result of poor cleaning. Although the drains were cleaned with a degreaser that is used for general cleaning, there was still significant soil on the drains even after they were cleaned. The high soil level likely reduced the performance of the sanitizers tested in this study.

The prior art does not provide a floor drain cleaner which can effectively control *Listeria*. Neither does the prior art provide a floor drain cleaner of this type which is easily applied to the drain.

The objects of the invention therefore are:

a. Providing an improved floor drain cleaner.

b. Providing a floor drain cleaner which substantially reduces the presence of *Listeria*.

c. Providing a floor drain cleaner of the foregoing type which is easily applied to a drain.

d. Providing a floor drain cleaner of the foregoing type which reduces the need to disassemble the drain and obviates contact with a drain.

e. Providing a floor drain cleaner of the foregoing type which provides competitive exclusion of bacteria in the drain.

f. Providing a floor drain cleaner of the foregoing type which is economical to use.

SUMMARY OF THE INVENTION

The foregoing objects are accomplished and the shortcomings of the prior art are overcome by the method of this invention which includes introducing into a drain wherein *Listeria* is present, a dilute composition containing a cleaning agent composed of a chlorinated caustic cleaner, a blend of surfactants, a hypochlorite and water. The introduction of the composition in the drain is effected for a period of time to reduce the presence of the *Listeria*.

In a preferred manner, the composition is introduced by a hose end dispenser which includes a foam nozzle.

In another preferred manner, the composition is introduced daily into the drain so as to comply with usage requirements.

In one aspect, the drain is rinsed with water after the introduction of the composition.

In another aspect, a sanitizer is introduced into the drain.

In yet other aspects, the composition is introduced at the rate in the range of about 1.5 to 3.0 gallons per minute, the composition is present in the drain for a period of about 30 seconds to 10 minutes, and the cleaning agent is present in the range of 1 wt %/o to 10 wt % and preferably 5 wt %.

DESCRIPTION OF THE PREFERRED EMBODIMENT

Figure 1:
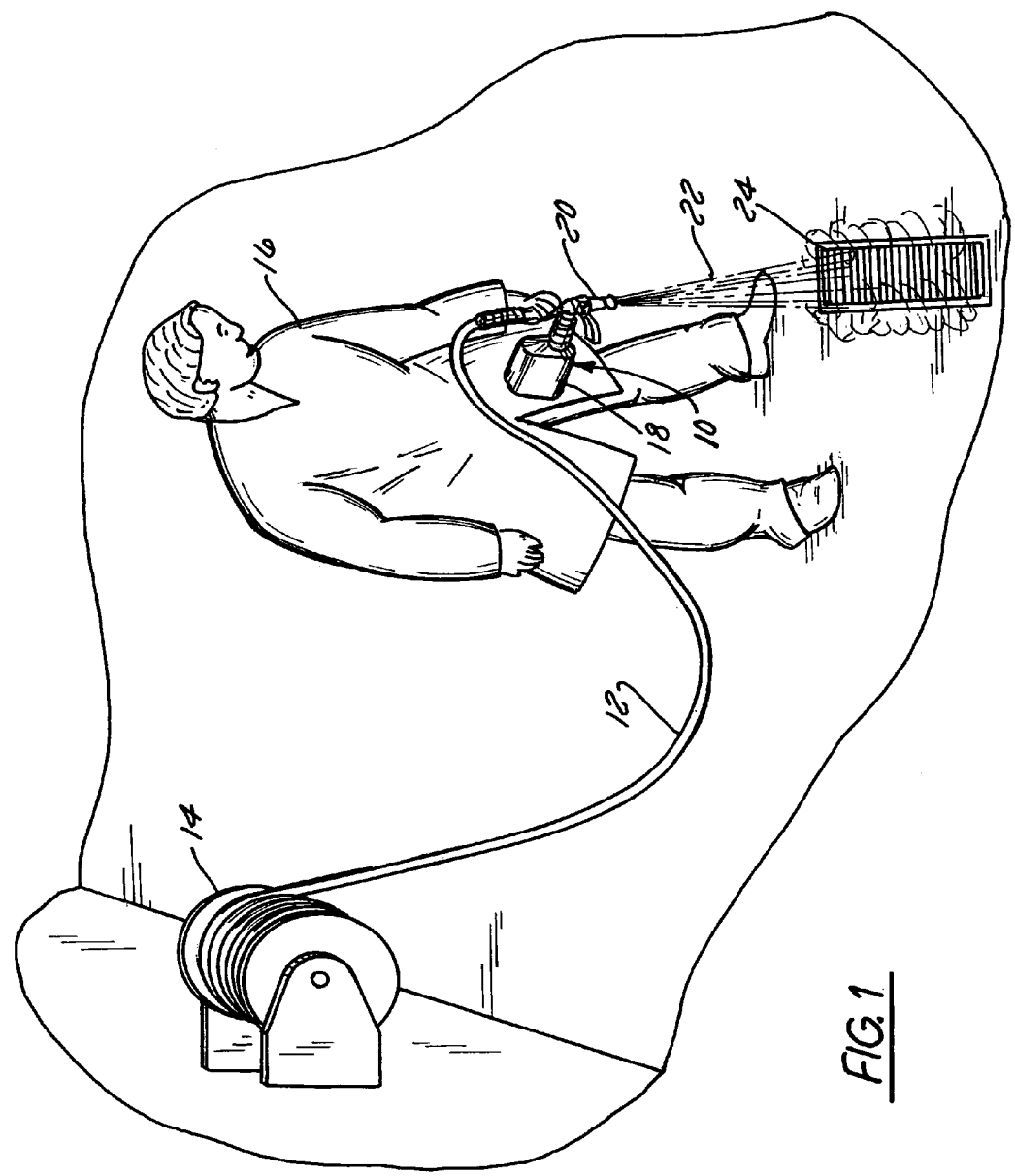
FIG. 1 is a pictorial view illustrating the method of this invention.

In order to examine the effect of cleaning on microbial levels in floor drains, the ability of two cleaners, a detergent based degreaser and a foaming caustic cleaner available from JohnsonDiversey, Inc. in Sturtevant, Wis. to reduce total microbial levels in floor drains were examined in a Racine cafeteria and in a manufacturing facilities cafeteria. The detergent based degreaser did not significantly reduce the total microbial populations in floor drains. However, a foaming caustic cleaner reduced total microbial CFUs by $1.5$–$2.0$ $\log_{10}$. In the test conducted the drains were treated by pouring the test solutions directly down the drains, waiting 60 seconds, rinsing thoroughly with water and immediately taking microbial samples.

The data collected suggested that using a foaming caustic cleaner could be a good way to reduce microbial levels, and possibly *Listeria*, in floor drains without using any hand scrubbing. Therefore, a study focused on controlling *Listeria* in the floor drains was initiated with the help of a retail chain store. By reducing or eliminating the organism in that location, it would help reduce the likelihood of *Listeria* accidentally contaminating a food contact surface, then contaminating food, and making someone ill. Based on data from the previous results, this study was focused on finding a way to improve cleaning of the floor drains and evaluating the ability of improved cleaning to reduce *Listeria* levels in the drain. The study was conducted in three stores identified as Stores A, B and C.

EXAMPLE 1

Drain Cleaning Practices in Retail Stores

A study was initiated by examining current drain cleaning practice at Stores A, B and C and conducting a discussion session with the retail chain store employees to determine what the customer desires were for the drain cleaning process and how the process could be improved. The current practice in the stores is that the drains should be cleaned on a daily basis. They need to be disassembled and the drain grates, liners, and any other components cleaned and scrubbed with degreaser, rinsed and sanitized. The drain itself is to be scrubbed with degreaser and a drain brush and then rinsed and sanitized. The drain is then reassembled. If this practice were followed every day it is possible that there would be little if any *Listeria* in the store's floor drains. However this practice is rarely followed for a number of reasons. There are practical issues with following this procedure. Some of the drains cannot be accessed because they are partially or completely underneath equipment that cannot be easily moved. Other drains cannot be accessed because the grates are either corroded or bolted in place.

In addition to all the problems accessing the drains, they are often intentionally not cleaned. A discussion held with the retail chain store employees indicated that the main issue that they had with cleaning the drains is that they did not want to touch them. Drains were seen as very unpleasant items to clean. They smelled bad, were very dirty, covered with biofilm, were difficult to clean, and were time consuming to clean. As a result, many drains were only rarely cleaned leading to a cycle of neglect. The drains were unpleasant and difficult to clean so they were ignored which made them even more unpleasant and harder to clean so they were ignored even more. If the drains were actually cleaned every day this job would likely be less unpleasant and so more likely to be done.

However, even if the drain cleaning were done, there were concerns expressed by the retail chain store food safety team that the current cleaning practices may have problems associated with them. Current practice calls for using a drain brush to scrub out the drains themselves. It is possible that using a brush may generate aerosols and could spread organisms such as *Listeria*, from deep in the drain into the food handling environment and could contaminate food contact surfaces.

As a result of the poor compliance with current cleaning practices and the concern that the current practice could spread potential pathogens through the retail environment, a way to improve cleaning while simplifying the process, minimizing the need for employees to touch the drains, and reduce the production of aerosols was needed for this study. When improving the cleaning of surfaces there are generally four variables that can be controlled. The time that is spent cleaning can be increased, the mechanical action can be increased, the chemicals used to clean can be more aggressive, or the temperature at which the cleaning is conducted can be raised. Three of these four variables were not options for this application. There is little spare time available to employees in a retail setting so it is difficult to increase the time spent cleaning. Even if the time were available, the discussions showed that the job is unpleasant enough that it is not likely to get done no matter how much time to do it was provided.

Increasing the mechanical action is also problematic. Not only would this require the employees to touch the drains and so reduce the likelihood that the procedure would be followed, increased mechanical action could increase the chance of spreading organisms from inside the drain to the retail environment. It is also not practical to increase the temperature at which the cleaning is done. Using very high temperature water would be a safety and cost issue for mainly retailers. Therefore the only variable that can be improved upon is cleaning chemical strength which is what we focused on.

EXAMPLE 2

Test Product

The foaming caustic cleaner has the following formula:

| Ingredient | Amount (%) |
|---|---|
| Deionized Water | 50.05 |
| Sodium Hypochlorite 12.5%* | 24.00 |
| Sodium Silicate Solution, 3.22/1 | 7.00 |
| Myristyl Amine Oxide | 5.20 |
| Potassium Hydroxide Liquid 45% | 4.60 |
| Sodium Tripolyphosphate (Regular Granular, medium TR) | 4.00 |
| Sodium Xylene Sulfonate, 40% | 2.50 |
| Tetrapotassium Pyrophosphate, 60% | 1.00 |
| ACUSOL 445* | 0.75 |
| Dodecyl Benzene Sulfonic Acid | 0.65 |
| Caprylic Acid CA1560 | 0.25 |

*Available from Rohn and Haas

The foaming caustic cleaner is a soft metal safe chlorinated caustic cleaner that is used for environmental and open plant cleaning at food processors. It also contains a specific blend of surfactants that cause it to cling to vertical surfaces longer than most foam cleaners. The hypochlorite is important for removing protein soil from surfaces and the high causticity makes it a good cleaner for fat and oily soils. Because many drains are made of soft metals like cast iron, pot metal, or brass it is important that this product be soft metal safe. The foaming caustic cleaner contains silicates to ensure that it will not be corrosive to soft metals. Because it does contain silicates however, it is important that it be rinsed thoroughly to prevent silicate build up on surfaces.

In order to overcome concerns about the safety of the foaming caustic cleaner product in a retail environment, it was packaged in a vented dispenser with a 1.5 l container. This vented dispenser is disclosed in U.S. patent application Ser. No. 10/876,056 filed Jun. 24, 2004, which is commonly owned, the teachings of which are incorporated by reference. It is herein referred to as Ready To Dispense (RTD). This assures the operator cannot come in contact at any time with the concentrate liquid. The dispensers were equipped with foaming nozzles, as described in U.S. patent application Ser. No. 10/605,133 filed Sep. 10, 2003 which is commonly owned, the teachings of which are incorporated by reference.

The method of the invention is illustrated in FIG. 1. The RTD dispenser generally 10 is shown connected to hose 12 and hose reel 14 to supply water to dispenser 10. The operator 16 is activating the dispenser 10 to cause water from hose 12 to pass through an eductor in the dispenser and draw the foaming caustic cleaner concentrate from the container 18 and mix it with the water. The diluted concentrate is delivered from a foam nozzle 20 in the form of a foam spray 22. The concentrate is introduced at the rate of 1.5 to 3.0 gallons per minute and is allowed to remain in the drain for 30 seconds to 10 minutes. It is directed into a drain 24 without having to disassemble the drain 24. In addition to providing added safety, using the RTD dispenser had several other advantages. No additional dosing or application equipment was required. By spraying the product from an RTD dispenser, it was easier to apply cleaner to drains under sinks or that were partially blocked by equipment. Using the RTD dispenser also assured that the product would be properly dosed at the required 5% concentration. However, this concentration can range from 1 wt % to 10 wt %. Finally, in using the RTD dispenser a "no touch" application was employed by eliminating hand mixing and application of cleaning solutions.

EXAMPLE 3

Test Schedule and Application Procedures

The study was conducted in the previously indicated stores designated A, B and C. There were two changes made to customer practices during this study. The procedure for cleaning the drains was changed and the chemical used to clean them was also changed. In order to differentiate between effects caused by changes in procedure and changes in cleaning chemicals, it was necessary to conduct the study in three phases. The first phase was collecting baseline data. During this phase there were no changes made to store practices. The procedures and chemicals they used were not changed. The store personnel were not encouraged to clean more frequently and, where practical, the store personnel who were cleaning the drains were not informed that microbiological samples of the drains were being taken. The baseline lasted for three weeks. After the baseline period, the drain cleaning practice was changed but the chemicals used were the same ones that the store had been using. The new practice was:

Remove large soil particles from the drain and around it if necessary.

If large chunks of soil are too big to go down the drain, disassemble the drain as necessary and remove them by hand.

Reassemble the drain if necessary.

Spray drains with degreaser long enough to ensure the entire drain, including the grate and sides, are thoroughly wet with foam. Do not spray for more than thirty seconds. If no spray apparatus is available pour sufficient use solution down the drain to ensure that all parts of the drain are wet with product.

Allow the cleaner to remain on the drain for 5 minutes.

Rinse drain thoroughly.

Apply sanitizer to the drain covering all surfaces.

Allow drain to dry; do not rinse with water.

Drains were cleaned daily during the regular cleanup for the departments in which they were located. This procedure was used for two weeks.

During the third phase of the trial, the procedure described above was used, however rather than using the degreaser that the store normally used; the foaming caustic cleaner was applied using the 1.5 l RTD dispenser equipped with the foam nozzles. No metering tip was used and the use concentration of cleaner was 5%. The application of the sanitizer remained constant. The final phase of the trial lasted two weeks.

EXAMPLE 4

Microbial Sampling and Analysis

Microbiological samples were taken from each store once per week. Microbiologic sampling was conducted in the mornings, several hours after the completion of cleaning and sanitizing. At the B & C stores, there were ten drains sampled. Two drains were sampled in five departments, meat, deli, seafood, bakery, and produce. There were three samples taken from each drain. The drains were a mixture of types ranging from catch basin drains under hand washing or three compartment sinks, to trench drains, or circular floor drains. There were three samples taken from each drain. One of the grate or as high in the drain as possible if there were no grate, another sample was the drain liner if there was one present, and the final sample was as deep in the drain as possible. The sample locations at the A store were a little bit different. The A store did not cut meat so in that store there were samples taken from two drains in the bakery, produce, seafood, and the hot food departments. One drain in the deli was sampled in the A store. Sample locations for each store are given in Tables 1–3 below.

TABLE 1

Sample sites for B store:

| Sample Number | Sample site |
|---|---|
| 1 | Bakery Cooler Drain Grate |
| 2 | Bakery Cooler Drain Strainer |
| 3 | Bakery Cooler Drain Inside |
| 4 | Bakery Circular Floor Drain Grate |
| 5 | Bakery Circular Floor Drain Basket |
| 6 | Bakery Circular Floor Drain Inside |
| 7 | Meat Cooler Drain Grate |
| 8 | Meat Cooler Drain Strainer |
| 9 | Meat Cooler Drain Inside |
| 10 | Meat 3 Compartment Sink Drain Side |
| 11 | Meat 3 Compartment Sink Drain Strainer |
| 12 | Meat 3 Compartment Sink Drain Inside |
| 13 | Seafood 3 Compartment Sink Drain Side |
| 14 | Seafood 3 Compartment Sink Drain Strainer |
| 15 | Seafood 3 Compartment Sink Drain Inside |
| 16 | Seafood Preparation Sink Drain Side |
| 17 | Seafood Preparation Sink Drain Strainer |
| 18 | Seafood Preparation Sink Drain Inside |
| 19 | Deli Circular Floor Drain Grate |
| 20 | Deli Circular Floor Drain Basket |
| 21 | Deli Circular Floor Drain Inside |
| 22 | Deli 3 Compartment Sink Drain Side |
| 23 | Deli 3 Compartment Sink Drain Strainer |
| 24 | Deli 3 Compartment Sink Drain Inside |
| 25 | Produce Cooler Drain Grate |
| 26 | Produce Cooler Drain Strainer |
| 27 | Produce Cooler Drain Inside |
| 28 | Produce Preparation Sink Drain Side |
| 29 | Produce Preparation Sink Drain Strainer |
| 30 | Produce Preparation Sink Drain Inside |

TABLE 2

Sample sites for C store

| Sample Number | Sample site |
|---|---|
| 1 | Produce trench cover |
| 2 | Produce trench side |
| 3 | Produce trench bottom |
| 4 | Produce 3 bay side |
| 5 | Produce 3 bay grate |
| 6 | Produce 3 bay bottom |
| 7 | Deli sandwich prep cover |
| 8 | Deli sandwich prep basket |
| 9 | Deli sandwich prep Bottom |
| 10 | Deli slicer cover |
| 11 | Deli slicer basket |
| 12 | Deli cover bottom |
| 13 | Seafood 3 bay side |
| 14 | Seafood 3 bay grate |
| 15 | Seafood 3 bay grate |
| 16 | Seafood rear cover |
| 17 | Seafood rear basket |
| 18 | Seafood rear bottom |
| 19 | Meat trench cover |
| 20 | Meat trench side |
| 21 | Meat trench bottom |
| 22 | Meat 3 bay side |
| 23 | Meat 3 bay grate |
| 24 | Meat 3 bay bottom |
| 25 | Bakery 3 bay side |
| 26 | Bakery 3 bay grate |
| 27 | Bakery 3 bay bottom |
| 28 | Bakery donut cover |
| 29 | Bakery donut basket |
| 30 | Bakery donut bottom |

TABLE 3

Sample sites for A store

| Sample Number | Sample site |
|---|---|
| 1 | Floor drain cover at cake deco station |
| 2 | Floor drain basket at cake deco station |
| 3 | Floor drain pipe wall at cake deco station |
| 4 | Bakery 3 bay sink drain basket. |
| 5 | Bakery 3 bay sink walls of drain. |
| 6 | Seafood floor drain cover. |
| 7 | Seafood floor drain basket. |
| 8 | Seafood floor drain pipe wall. |
| 9 | Seafood prep sink drain basket |
| 10 | Seafood prep sink walls of drain |
| 11 | Hot food floor drain cover at chicken prep ovens |
| 12 | Hot food floor drain basket at chicken prep ovens |
| 13 | Hot food floor drain pipe wall at chicken prep ovens |
| 14 | Hot food 3 bay sink drain basket |
| 15 | Hot food 3 bay sink walls of drain |
| 16 | Deli floor drain cover. |
| 17 | Deli floor drain basket. |
| 18 | Deli floor drain pipe wall. |
| 19 | Produce floor drain cover. |
| 20 | Produce floor drain basket. |
| 21 | Produce floor drain pipe wall. |
| 22 | Produce prep sink drain basket |
| 23 | Produce prep sink walls of drain |

Samples were taken using sterile sponges that had been soaked with a neutralizing buffer. One sponge was used for each sample and the sponge was rubbed on all surfaces of the site being sampled. The sponges were returned to the sterile bags they came in and packed into an insulated container with ice packs to keep the samples cold during shipping.

Samples taken the first two weeks were sent to Johnson-Diversey laboratories in Racine where they were analyzed for Aerobic Plate Counts (APCs). The APC for each sample was determined by expressing at least 1 ml of buffer from the sample sponge. The buffer was diluted as appropriate in Butterfield's phosphate buffer and the bacteria enumerated by plating on APC Petrifilm (3M) according to manufacturers instructions. The Petrifilms were placed in a 32° C. incubator for 48 hours after which time the colonies counted.

Samples taken after the first two weeks were sent to a microbiology laboratory where the samples were analyzed for APC and for generic *Listeria* counts. The APC procedure followed at the outside testing lab was the same as followed at JohnsonDiversey. The *Listeria* counts were determined by spread plating the samples on Modified Oxford agar plates (MOX agar). *Listeria* counts were conducted on the $10^1$ through the $10^2$ dilutions as well as undiluted buffer from the sponge. The undiluted buffer was tested by plating 0.5 ml on each of 4 MOX agar plates. APC and MOX agar plates were all incubated at 32° C. When the MOX agar plates were counted, only those colonies displaying typical *Listeria* appearance were counted. No further identification of *Listeria* was done so it is not known what species of *Listeria* were present in the samples.

RESULTS

Test Product Cleaning and Consumption Rates

The feed back from those who used the foaming caustic cleaner at the C store was generally positive. They thought it was a good product. The drains appeared cleaner when the foaming caustic cleaner was used, however it is not possible to tell if that was due only to the product or to people simply paying more attention to cleaning because the study was being conducted.

Feedback from the A store test site was that the foaming caustic cleaner in the RTD dispenser was easy to use. According to one observer the drains on which the foaming caustic cleaner was used "looked like new".

All of the test product was consumed at the C store. This was 10 1.5 l bottles used on ten drains each night over a two week period. The consumption rate at the B store was more variable with some departments appearing to use a lot of product and others very little. It is possible that the same bottles may have been used to clean drains in several departments.

Figure 2:
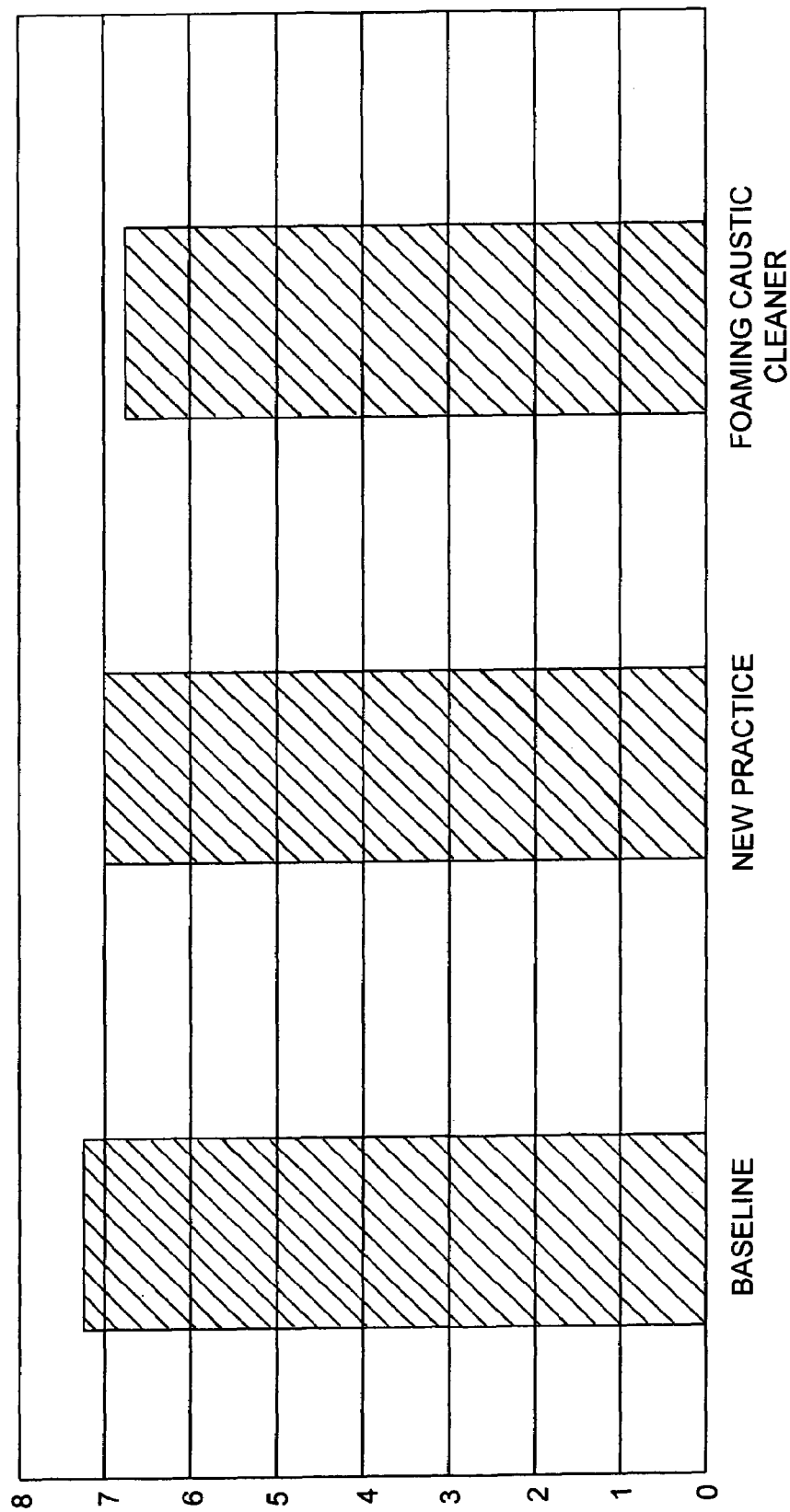
FIG. 2 is a bar graph illustrating Aerobic Plate Counts for three tests.

Microbiology Results:

FIG. 2 shows the average APC $Log_{10}$ CFU for the two week baseline, two weeks in which the cleaning practice was simplified but the cleaners used were the ones that the stores currently employ, and the final two weeks when the foaming caustic cleaner was used along with the simplified procedure. Data shown is the average of all samples from all stores for each of the three treatments. The average APC levels observed during the treatment with the foaming caustic cleaner was significantly ($\alpha=0.05$) lower than that observed during the baseline period.

Figure 3:
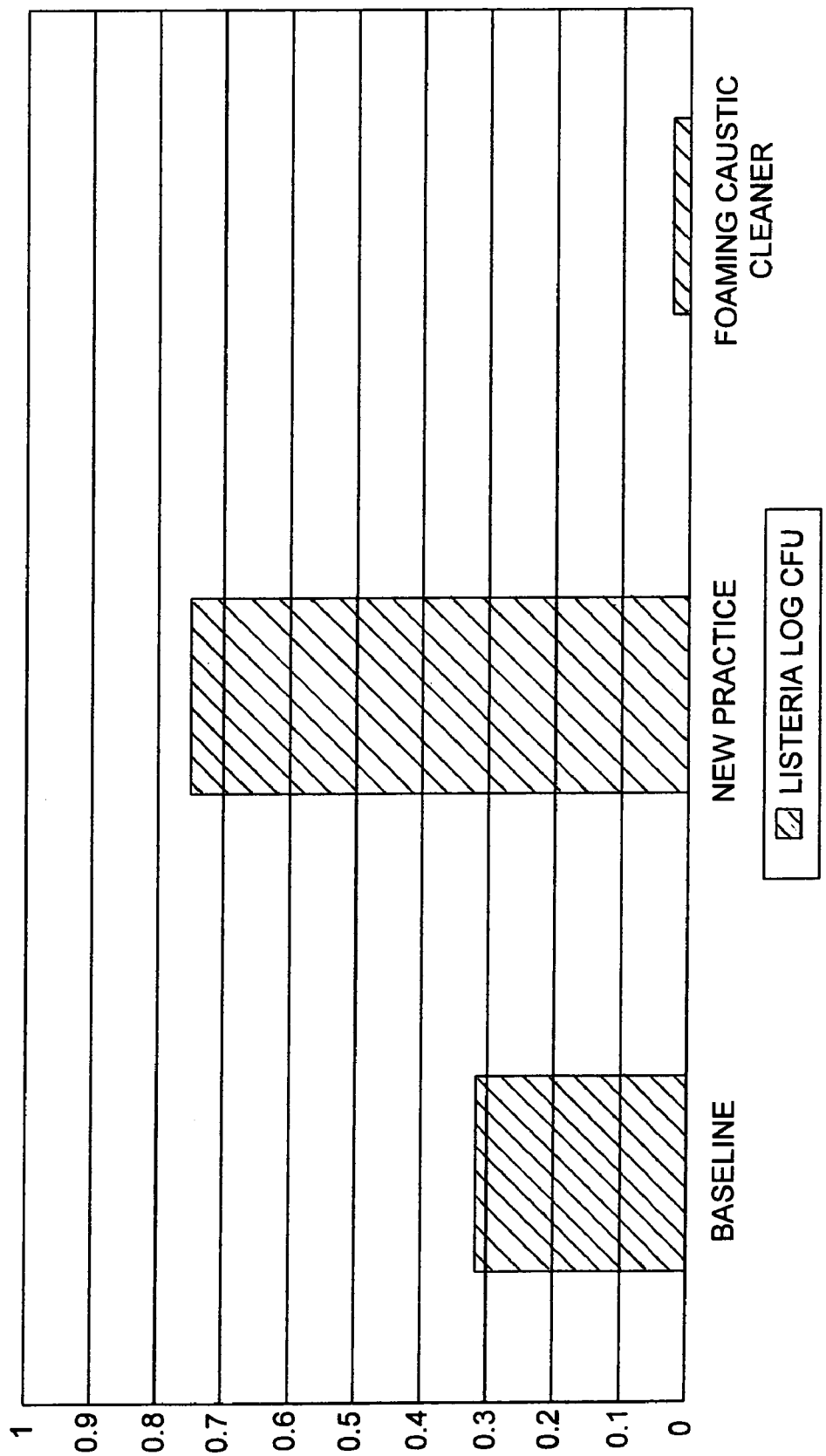
FIG. 3 is a bar graph illustrating *Listeria* counts for three tests.

FIG. 3 shows the average *Listeria* $Log_{10}$ CFU for the same time period. The *Listeria* levels observed during the middle phase of the test when the new simplified cleaning procedure was used with the stores existing chemistry was significantly ($\alpha=0.05$) higher than either of the other test conditions. The *Listeria* counts observed during the foaming caustic cleaner testing was significantly ($\alpha=0.05$) lower than that observed when the other cleaning regimens were used.

*Listeria* counts were more sporadic than the APC counts. Not every sample was positive for *Listeria*. During the one week of baseline collection that *Listeria* evaluations were performed, and the two weeks when new practice but the current store chemistries were used, approximately ⅓ to ⅔ of samples were positive for *Listeria*. The counts on those positive samples ranged from about 1 to 3 $log_{10}$ CFU per ml. Table 4 summarizes the percentage of positive *Listeria* samples per store per week and the average counts of those positive samples.

TABLE 4

Listeria data summary.

| Store | 1/Baseline | 2/New practice | 3/New practice | 4/Foaming caustic cleaner | 5/Foaming caustic cleaner |
|---|---|---|---|---|---|
| | Percent of samples positive for Listeria/average Log CFU of Listeria positive samples | | | | |
| A | 33%/1.86 | 43%/2.05 | 57%/1.19 | 4%/0.85 | 0%/0.0 |
| B | 3%/1.0 | 20%/2.79 | 30%/1.07 | 0%/0.0 | 0%/0.0 |
| C | 16%/2.39 | 60%/2.09 | 60%/1.45 | 10%/1.17 | 0%/0.0 |

The microbial levels observed in floor drains in the foregoing study are typical of what has been observed in previous studies. Floor drains general have from $10^4$ to $10^9$ total organisms on and around the drains. That was the level observed in this study. The presence and level of *Listeria* observed in this test is also similar to what was seen in previous studies. *Listeria* was present, but it was far more sporadic and was only present in 30–60% of samples (depending on treatment). When the organism was present it was general found at the 1–2 $log_{10}$ CFU level. Again that frequency and those levels were similar to what had been observed in previous studies.

The reduction in APCs (approximately 0.5 log) was not as large as was seen when the foaming caustic cleaner was tested in Racine (1.5–2.0 log), however it should be noted that the samples in Racine were taken immediately after treatment with the foaming caustic cleaner, while the samples at the A, B & C stores were taken approximately 12 hours after the drains had been treated. This is more than sufficient time for the surviving organism to have grown back to nearly the levels they were prior to treatment. On the other hand, the reduction observed in the A, B & C store study is very similar to the reductions observed in the samples taken in the Racine study 24 hours after drain treatment with the foaming caustic cleaner (0.3–0.5 log reduction). This also supports the hypothesis that the surviving organisms grow back relatively quickly after drain treatment.

The total aerobic plate count reduction of 0.4 Log and the *Listeria* species log reduction of 1.5 at first glance may appear contradictory. *Listeria* is not a particularly difficult organism to kill. It is not resistant to cleaners or sanitizers, therefore it is reasonable to assume that *Listeria* would be reduced by the same level as most other microorganisms present in the drains. The Racine study indicated that the foaming caustic cleaner would deliver a 1.5–2 log reduction of total microorganisms present in the drains. Therefore it is logical to assume that the *Listeria*, present in the 1.5–2 log range, could be completely eliminated by this treatment. Therefore, when the microbiology samples were taken during the A, B & C store study, twelve hours after cleaning, the total number of microorganisms had re-grown to nearly the same levels they were at before cleaning. *Listeria* was not able to recover however, because that particular organism had been completely eliminated by the cleaning process.

A healthy bacterial population in the drains may contribute towards keeping the system *Listeria* free with the proposed treatment. The foaming caustic cleaner appears to cause the *Listeria* to be displaced by the other organisms that are present in larger numbers. This is known as competitive exclusion. The continued presence of high levels of microorganisms in the drains could help prevent *Listeria* recolonizing the drains. It is not clear from this study how often the drains will need to be cleaned to keep them free of *Listeria*. It may not be necessary to clean them every day as was done in this trial.

The consumption rate varied considerably during this study. At one site several 1.5 l bottles of test product were used up in one evening but this was likely a mistake and the test product was used as a general degreaser rather than just to treat the test drains. In another test site it almost looked as though the product was not being consumed at all, although the elimination of *Listeria* at that site suggests that it was being applied to the drains. The packages of test product are easy to move from site to site within a store so it may have just been a case of a bottle from one department being used to clean other locations. For a typical drain, one should be able to effect proper treatment by applying approximately 250–500 ml of in-use solution of the foaming caustic cleaner. This is equivalent to approximately 25 mL of the foaming caustic cleaner per use which, with daily application, translates to about a quarter to half a bottle per drain/month.

During the previously described trials, the use of the foaming caustic cleaner was followed by rinsing and then application of a sanitizer to the drains. It is unclear that the use of a sanitizer was needed to control *Listeria*. The sanitizer was used along with Prime Cult Ultra or Break Up available from JohnsonDiversey, Inc. in Sturtevant, Wis. These are heavy duty cleaners and were used during the second phase of the study. There was little or no reduction of microorganisms during that time, in fact *Listeria* numbers increased. The reduction in *Listeria* and general microbial levels when the foaming caustic cleaner was used suggests that the use of a sanitizer may not be necessary.

It is recognized that people did not want to have to touch the drains. This simplified system using a more aggressive cleaner largely addresses that requirement. The use of the foaming caustic cleaner does not completely eliminate the need to touch the drains. If there are large particles of soil in the drain those must still be removed by hand to ensure that the drain remains free flowing, however if the drain is not clogged then there is no need for employees to touch it. The use of an aggressive foam cleaner with extend contact time also eliminates the need to use drain brushes or other tools that may spread contamination around a retail setting. By dispensing the product out of a package like the RTD dispenser, the foaming caustic cleaner is relatively easy to use and it is easier to apply to drains in hard to get to places like under sinks.

During the previously described trials, the drains were cleaned every night. Prior to the study the drains were cleaned on a relatively infrequent basis. This was largely a result of drain cleaning being an unpleasant job because the drains had to be disassembled by hand and were often difficult to access. This simplified drain cleaning procedure does not require drain disassembly, is faster, and minimizes the need for employees to touch the drains will be preformed on a more frequent basis than the old cleaning process.

The foaming caustic cleaner has been described as the preferred drain cleaner. However other drain cleaners which are soft metal compatible, contain chlorinated caustics and have a viscosity profile to be dispensed from a hose end dispenser and remain in contact with the drain for 30 seconds to ten minutes could be employed.

It will thus be seen that there is now provided a simplified, minimal-touch procedure to eliminate *Listeria* from the floor drains. The procedure improved the visual cleanliness of the drains and they were able to be cleaned with minimal contact and without disassembling them. Competitive exclusion of *Listeria* is also provided.

What is claimed is:

1. A method of controlling *Listeria* in drains comprising:
   introducing into a drain wherein *Listeria* is present, a dilute foamable composition containing a cleaning agent comprising:
   a. a caustic cleaner
   b. a blend of surfactants
   c. a hypochlorite; and
   d. water
   the introduction of the composition in the drain being effected by a hose end dispenser including a foam nozzle for a period of time from about 30 seconds to 10 minutes to reduce the presence of the *Listeria*.

2. The method of claim 1 wherein the composition is introduced daily into the drain.

3. The method of claim 2 wherein the composition is introduced into the drain for a period of two weeks.

4. The method of claim 1 wherein the drain is rinsed with water after the introduction of the composition.

5. The method of claim 4 further including the introduction of a sanitizer into the drain.

6. The method of claim 1 wherein the composition is introduced at the rate in the range of about 1.5 to 3.0 gallons per minute.

7. The method of claim 1 wherein the composition is present in the drain for a period of about 30 seconds to 10 minutes.

8. The method of claim 1 wherein the composition further includes silicates.

9. The method of claim 1 wherein the cleaning agent is present in the range of 1 wt % to 10 wt %.

10. The method of claim 1 wherein the composition is introduced into the drain without disassembly thereof.

11. The method of claim 1, wherein the cleaning agent is present in the amount of 5 wt %.

\* \* \* \* \*